(12) United States Patent
Terui et al.

(10) Patent No.: US 6,333,760 B1
(45) Date of Patent: Dec. 25, 2001

(54) AREA ISOLATION TYPE SOLID-STATE IMAGE PICKUP DEVICE FOR INCREASING THE USAGE OF THE ELEMENT FORMATION SURFACE OF A SEMICONDUCTOR CHIP

(75) Inventors: Takashi Terui; Tadashi Sugiki, both of Yokohama (JP)

(73) Assignee: Kawasaki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/035,832

(22) Filed: Mar. 6, 1998

(30) Foreign Application Priority Data

Mar. 6, 1997 (JP) .................................... 9-051694

(51) Int. Cl.⁷ .............................. H04N 3/14; H04N 5/225
(52) U.S. Cl. .......................... 348/315; 348/222; 348/247; 348/310; 348/340
(58) Field of Search ................................ 250/208.1, 215, 250/216; 257/414, 431, 432, 433; 340/937, 936, 933; 348/143, 148, 149, 207, 218, 272, 275, 294, 311, 315, 335, 340, 343, 344, 369, 373, 374; H04N 3/14, 7/18, 5/225

(56) References Cited

U.S. PATENT DOCUMENTS

| | | | |
|---|---|---|---|
| 4,958,223 | 9/1990 | Juvinall et al. ...................... 348/127 |
| 5,172,235 | * 12/1992 | Wilm et al. ........................... 348/149 |
| 5,235,656 | 8/1993 | Hilgeman .............................. 382/100 |
| 5,251,038 | * 10/1993 | Hirota .................................. 348/340 |
| 5,272,535 | 12/1993 | Elabd .................................. 348/314 |
| 5,452,004 | * 9/1995 | Roberts ................................ 348/301 |
| 5,940,126 | * 8/1999 | Kimura ................................ 348/218 |
| 5,956,087 | * 9/1999 | Takayama et al. ................... 348/315 |
| 6,172,351 | * 1/2001 | Kimura .............................. 250/208.1 |
| 6,172,361 | * 1/2001 | Holberg et al. .................... 250/208.1 |

FOREIGN PATENT DOCUMENTS

| | | | |
|---|---|---|---|
| 0 366 008 | 5/1990 | (EP) | ................................ H04N/5/33 |
| 2 240 444 | 7/1991 | (GB) | ................................ H04N/3/14 |
| 5-344428 | 12/1993 | (JP) | ............................... H04N/5/335 |
| 94/07287 | 3/1994 | (WO) | ................................ H01S/3/19 |

* cited by examiner

Primary Examiner—Wendy R. Garber
Assistant Examiner—Ngoc-Yen Vu
(74) Attorney, Agent, or Firm—Pillsbury Winthrop

(57) ABSTRACT

An area-isolation type solid-state image pickup device is such that an image pickup area is formed on an element formation surface of a semiconductor chip in a way to correspond to an optical image configuration of a subject, the semiconductor chip serving as an image pickup element, and an element drive circuit area and signal processing circuit area formed on a section other than the image pickup area. By doing so it is possible to fully utilize elements on an element formation surface of a semiconductor chip without ruining the element and hence to improve an efficiency with which a semiconductor device is manufactured.

6 Claims, 4 Drawing Sheets

AREA ISOLATION TYPE SOLID-STATE IMAGE PICKUP DEVICE FOR INCREASING THE USAGE OF THE ELEMENT FORMATION SURFACE OF A SEMICONDUCTOR CHIP

BACKGROUND OF THE INVENTION

The present invention relates to an area isolation type solid-state image pickup device capable of effectively utilizing its semiconductor chip by dividing an element formation surface of the semiconductor chip into different signal processing areas.

A general solid-state image pickup device is such that its image pickup surface constitutes an area satisfying a standard television's aspect ratio. And is an image pickup element, its drive circuit and an image pickup signal processing circuit are each comprised of an independent IC chip.

As a camera, however, some types not necessarily require any image pickup area satisfying the standard television's aspect ratio, such as an industrial monitoring camera used for the purpose of monitoring only a subject of a given configuration for instance. Some industrial inspection cameras are adapted to inspect a bottle for instance. The camera taking a shot of a bottle is such that, in its image pickup element, an area on which an optical image of a subject is formed is part of its whole area and, in this case, the rest of the area is not used effectively.

In recent years, the semiconductor integration techniques have been markedly advanced to enable more and more elements to be formed on the element formation surface of a semiconductor chip. If consideration is paid to the effective use of such a semiconductor chip, more area has not been effectively used.

BRIEF SUMMARY OF THE INVENTION

It is accordingly the object of the present invention to provide an area isolation type solid-state image pickup device which enables more elements to be effectively used on the element formation surface of a semiconductor chip and, by doing so, can achieve an improvement in the manufacturing efficiency of semiconductor products.

In order to achieve the above-mentioned object of the present invention, an image pickup area is formed on an element formation surface of a semiconductor chip in a way to correspond to an optical image configuration of a subject, the semiconductor chip serving as an image pickup element, and an element drive circuit as well as a processing section for processing a signal obtained from the image-processing area is formed on a section other than the image pickup area. By the above-mentioned means, more elements can be effectively used on the image pickup area and it is possible to improve the manufacturing efficiency of semiconductor products. Further, processing is made on an image pickup signal from a requisite minimal area, so that the burden of the signal processing section is alleviated.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of the present invention will be explained below with reference to the accompanying drawings.

Figure 1:
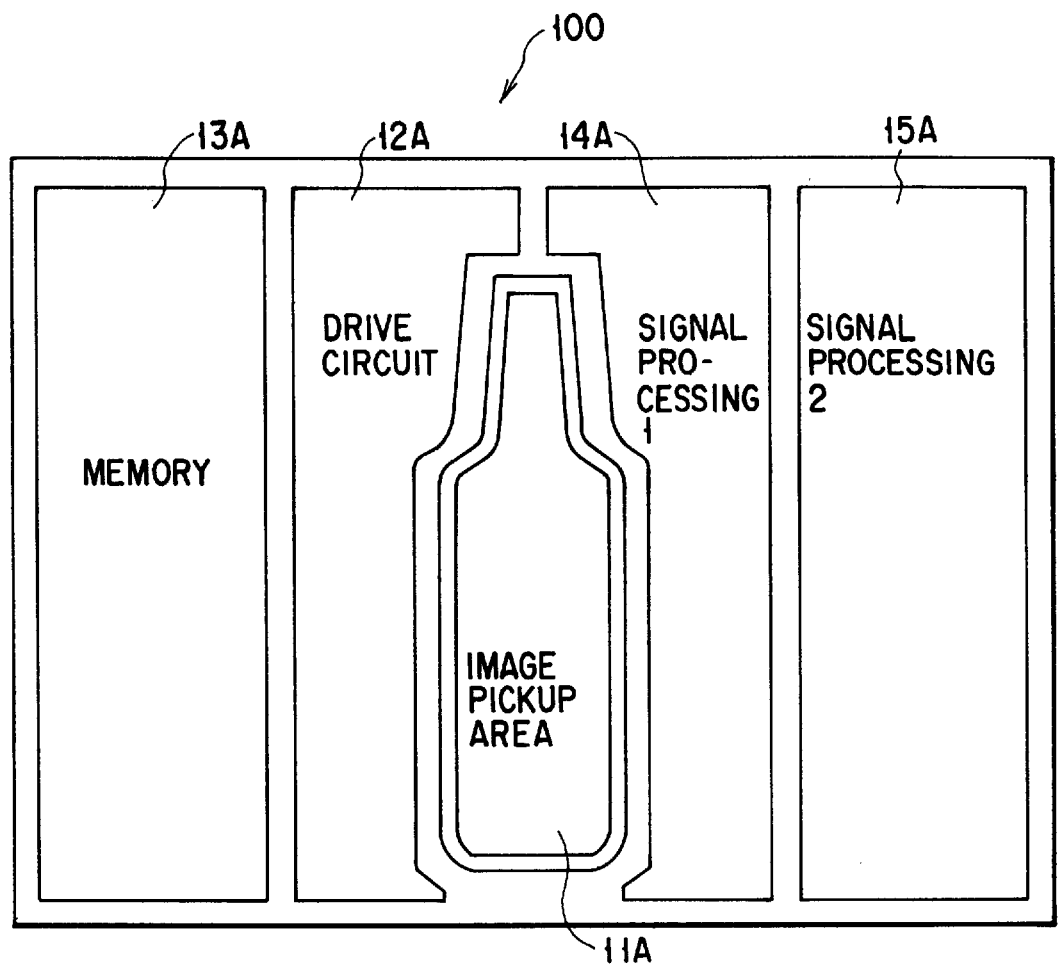
FIG. 1 is an explanatory view showing an arrangement of a semiconductor chip in a solid-state image pickup device according to one embodiment of the present invention.

FIG. 1 shows one embodiment of the present invention. Reference numeral 100 shows a semiconductor chip of a solid-state image pickup device according to one embodiment of the present invention. An image pickup area 11A is secured, for example, at a center section on an element formation surface of the semiconductor chip 100 to provide an image pickup section. The image pickup area 11A corresponds to a configuration of an optical image of, for example, a bottle in an upright state.

The image pickup device will be explained below as being used as a device for detecting, for example, a state of the bottle on a conveying path, that is, detecting whether or not there is any defect on the bottle.

A drive circuit area 12A is secured to the left side of the image pickup area 11A to provide a drive circuit and a memory area 13A is secured to the left side of the drive circuit area 12A to provide a memory. Further, a first signal processing circuit area 14A is provided to the right side of the image pickup area 11A and a second signal processing circuit area 15A is secured to the right side of the signal processing circuit area 14A. By doing so, these signal processing circuit areas provide signal processing circuits.

Figure 2:
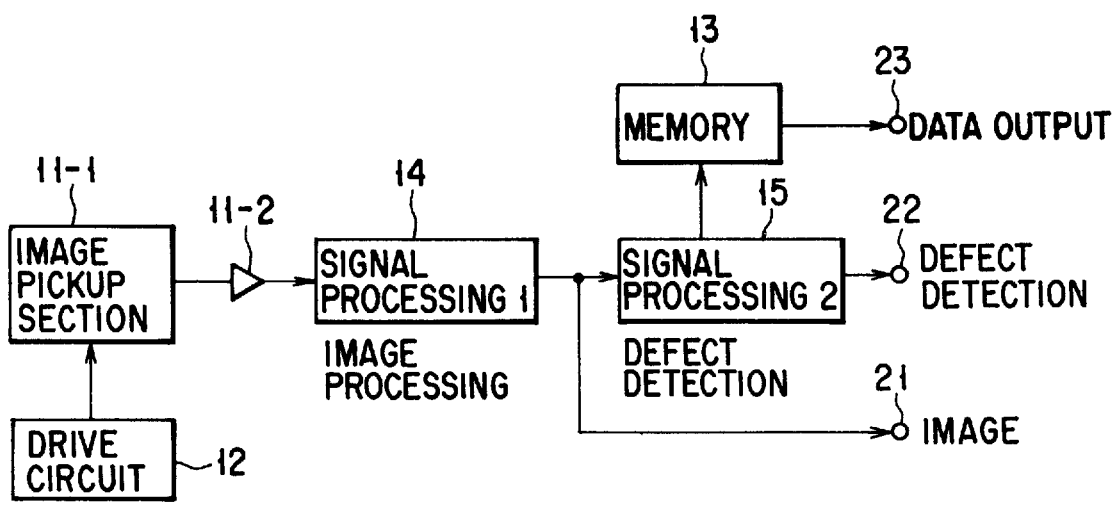
FIG. 2 is an explanatory view showing a circuit block on a semiconductor chip in FIG. 1.

FIG. 2 shows the connected states of the respective circuits structured on the above-mentioned areas.

The image pickup area 11A includes an image pickup section 11-1 and an amplifier 11-2 for amplifying a signal output from the image pickup section 11-1. A drive circuit 12 built in the drive circuit area 12A drives the image pickup section 11-1 and effects a digital shutter operation and image signal reading operation. An image pickup signal output from the amplifier 11-2 is supplied to a first signal processing circuit 14 built in the first signal processing circuit area 14A. The first signal processing circuit 14 converts an image picked-up signal to a standard video signal. By doing so, the video signal output from the signal processing circuit 14 is fed to an output terminal 21 and can be monitored at a monitor.

The video signal output from the first signal processing circuit 14 is supplied to a second signal processing circuit 15 built in the second signal processing circuit 15A. The second signal processing circuit 15 decides whether or not the picked-up signal forms a given image configuration, for example, detects any defect in or on the bottle or any label on the bottle.

In the case where any defect is to be detected or any label is to be identified, it is possible to compare the picked-up video data against reference video data stored in the device and perform an associated subtraction operation.

When any defect is detected on the bottle, the detected data is sent to a memory 13 in the memory area 13A where defect/no-defect information is stored. The signal, being detected as involving a defect on the bottle, emerges at the output terminal 22. In the case of the bottle being a "rejected" one, a flashing device for example is flashed ON and OFF or corresponding information is sent to a bottle sorting device where it is used for sorting a bottle into a defective or no-defective (good) one. For example, the defect/no defect information and identification information, etc. of bottles are written in the memory 13. As the bottle identification information there is a bar code on the label, for example, and its read-out data and defect/no defect information are stored as a pair. The data in the memory 13 is read out, as required, via the output terminal 23.

A sensor having such a structure is located at a plurality of places on the conveying path and can check every detail of the bottle at different angles. Or it is possible that the bottle is turned by a conveying device and checked by one sensor in a time-division fashion.

Figure 3:
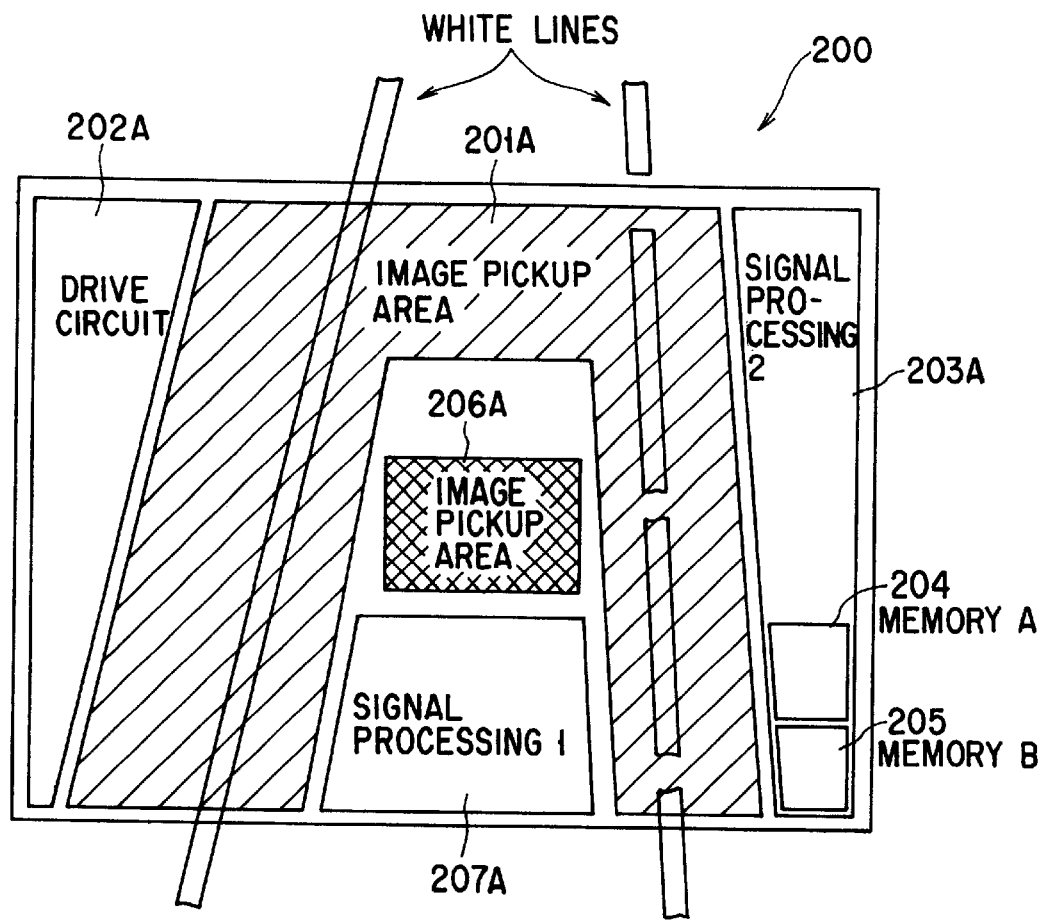
FIG. 3 is an explanatory view showing a semi-conductor chip in a solid-state image pickup device according to a second embodiment of the present invention.

FIG. 3 shows another embodiment of the present invention.

Reference numeral 200 shows a semiconductor chip and an image pickup area 201A as cross-hatched in FIG. 3 is secured, at a central area for example, on an element formation surface. The image pickup area 201A is, for example, of a non-inverted U-shaped type. This image pickup element is of a type such that, in an automatic running system of an automobile, it is adapted to detect white lines (traffic lines) on the vehicle road. The white lines, upon being shot with a camera, are acquired as right/left white lines on an image pickup plane as shown in FIG. 3 with their upper-side white lines' interval narrowed. As a necessary minimal image pickup area 201A an inverted U-shape or an inverted V-shape is fitted.

A drive circuit area 202A is secured to the left of the image pickup area 201A and a second signal processing circuit 203A is to the right side of the image pickup area 201A. Memories 204 and 205 are built in the signal processing circuit area 203A.

A second image pickup area 206A is secured inside the U-shaped image pickup area 201A, that is, between the U-shaped leg sections. Further, a first signal processing circuit area 207A is secured.

Figure 4:
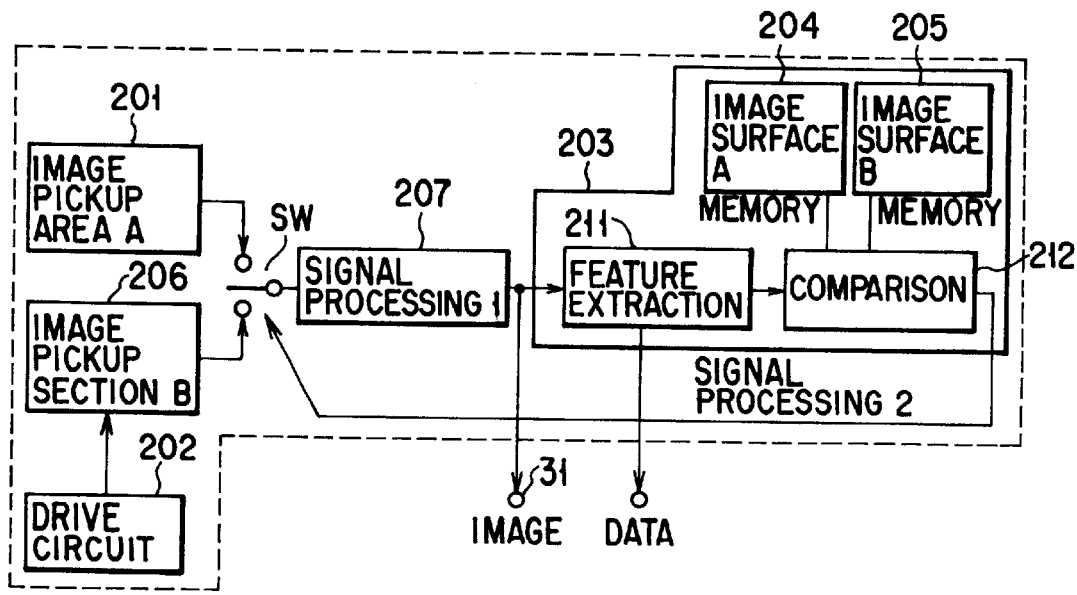
FIG. 4 is an explanatory view showing a circuit block on a semiconductor chip in FIG. 3.

FIG. 4 shows a connection configuration of a circuit in the semiconductor chip 200. Any one of image signals of image pickup sections 201 and 206 are selected by a switch SW and input to a second signal processing circuit 207 and converted to a standard video signal. The output signal of the second signal processing circuit 207 is derived from a terminal 31 and can be seen on a monitor. That output signal is input to a feature extraction circuit 211 in a first signal processing circuit 203. The feature extraction circuit 211 detects an edge of a white line image for example and a corresponding detected signal is supplied to a comparator 212.

With the image area 201A now selected by the switch SW, the comparator 212 compares edge information of the white line image with the information of the image memory 204 and decides whether or not the white line image is present within the image pickup area 201A. If the white line is present in an image pickup area 201A, the comparator 212 maintains the switch SW as it is. If the white line image is out of sight from the image pickup area 201A, the comparator 212 controls the switch SW by which switching is made to allow an image pickup signal which comes from the image pickup area 206A to be processed. As in the case of the image pickup area 201Af an optical image coming from a vehicle's front-facing optical system is conducted also to the image pickup area 206A. As will be set out below in more detail, an optical image from a vehicle's front-facing first optical system is conducted to the image pickup area 201A and an optical image from a vehicle's front-facing second optical system is conducted also to the image pickup area 206A. That is, the first and second optical systems differ in their magnifications in which case a lens on the second optical system is wider in its visual field than that on the first optical system. That is, the optical image conducted to the image pickup area 206A corresponds to a still farther optical image. Even if the white line is out of sight from the image pickup area 201A, there is sometimes the case where the white line image is conducted to the image pickup area 206A. The feature detection signal corresponding to a video signal at this time of a shot is also conducted to a comparator 212 and, this time, compared with the data of the image memory 205. When a white line image is detected, the vehicle is automatically steered to allow the white line image to be set to a predetermined position.

When the white line image is stably set to the predetermined position the comparator 212 enables the switch SW to be controlled and shifting to be made to a monitoring state of an enlarged image. After the shifting is so made, control information is created for an automatic driving device in response to the shaking of the white line image so as to achieve automatic steering.

As set out above, the configuration of the image pickup area is set in accordance with the configuration of a subject image and, by doing so, it is possible to effectively utilize the element formation surface of the semiconductor chip. The present invention can also be applied to a traffic monitoring system capable of taking a shot of a vehicle's driver and number plate. In this way, restriction is made on those shot areas where the driver's image and number plate's image are focused.

Figure 5:
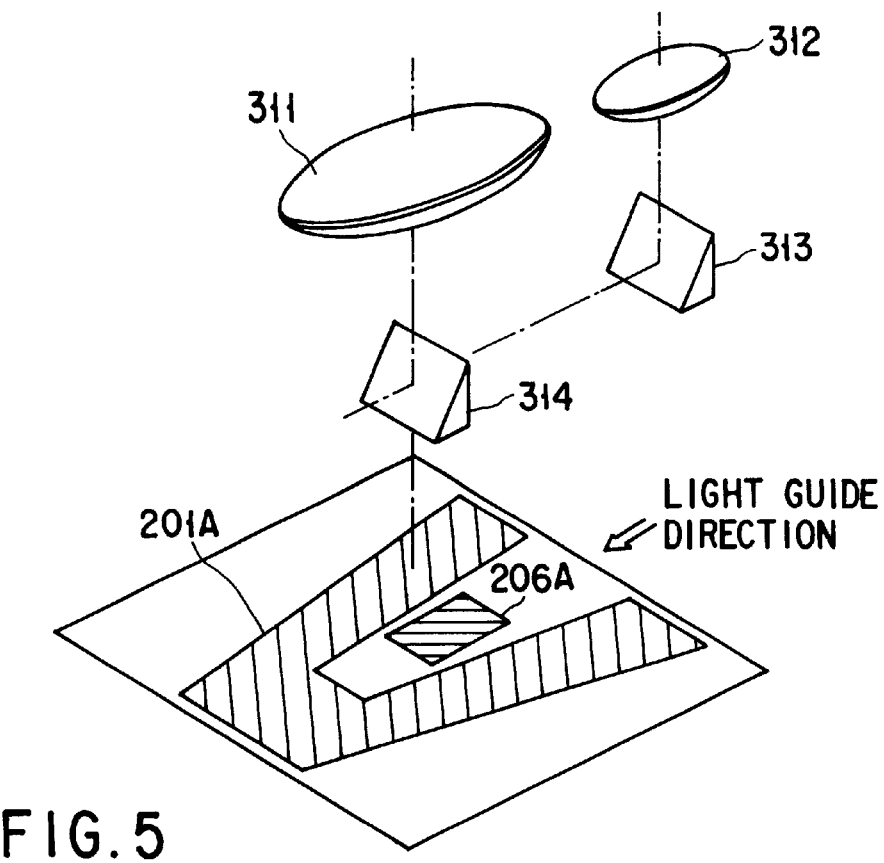
FIG. 5 is a view showing a schematic form of an optical system for conducting an optical image to an image pickup area in FIG. 3.

FIG. 5 shows a practical schematic form of an optical system for conducting optical images to the image pickup areas 201A and 206A in FIG. 3. An image pickup lens 311 is used to conduct a corresponding optical image to the image pickup area 201 and is arranged in a way to set an optical axis in coincidence with a center axis on a plane of the image pickup element 200. An optical image from an image pickup lens 312 is guided via a half mirror 313 and half mirror 314 to the image pickup area 206A. The image pickup lens 312 is wider in angle than the image pickup lens 311 and is of a telescopic type. In order to prevent any interference of light from the image pickup lens 311, the mirrors 313 and 314 are so arranged as to allow light to be conducted from a direction corresponding to an opening side of the U-shaped type image pickup area 201A.

Figure 6:
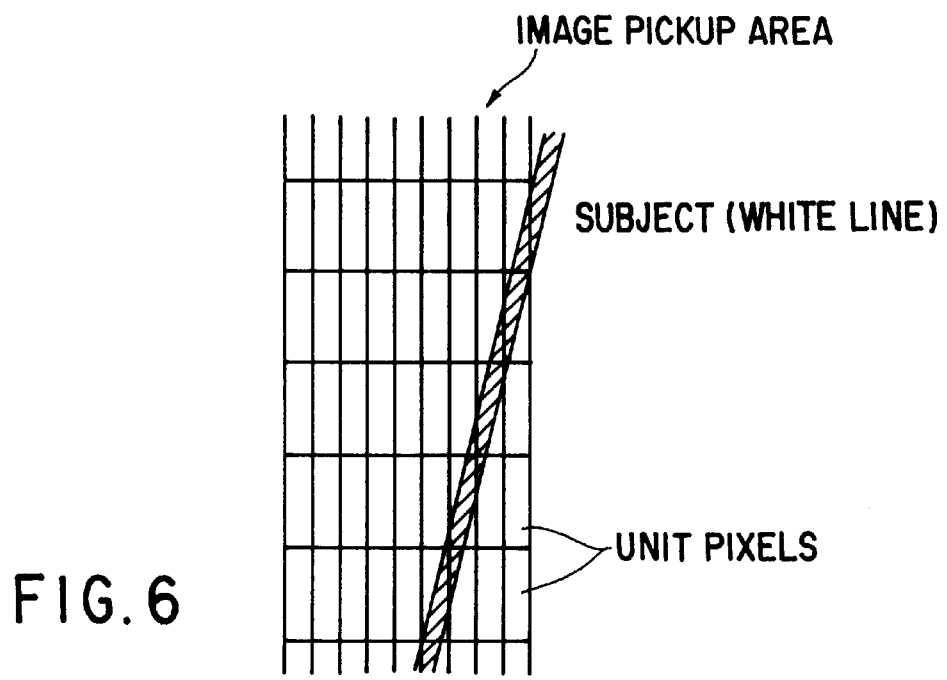
FIG. 6 is a view showing a pixel array of an image pickup.

FIG. 6 shows an example of a pixel array of an image pickup area suitable to the detection of the above-mentioned white line image. In the case where the running of the vehicle is to be controlled by taking a shot of a front-side white line image, it is important to judge the moving to a lateral direction of the white line image on the image pickup area, but the longitudinal direction of the white line image is not so important to judge. It is advantageous to use a pixel array with a unit pixel longer in the longitudinal direction and shorter in the lateral direction as shown in FIG. 6. If, on the other hand, it is important to monitor an object longer in the lateral direction and shorter in the longitudinal direction, it may be possible to create a unit pixel longer in its lateral direction.

Figure 7:
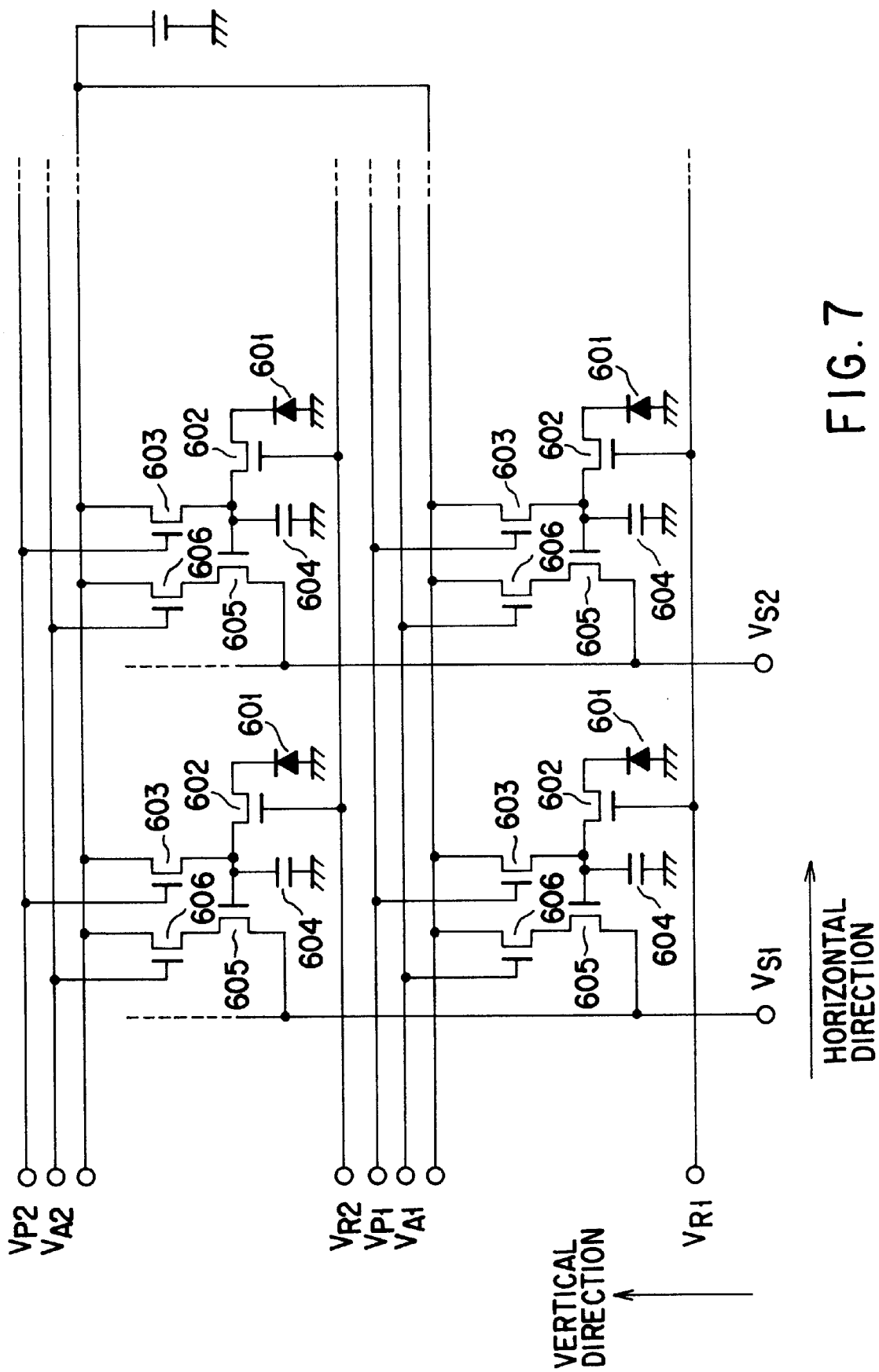
FIG. 7 is a view showing a circuit arrangement of an image pickup area.

FIG. 7 shows a schematic circuit arrangement of an image pickup area.

In the image pickup array, one pixel comprises a photodiode 601, signal readout transistor 602, a reset transistor 603, charge voltage conversion capacitor 604, signal amplifying transistor 605 and row select transistor 606. Since each pixel is the same in configuration, those elements constituting a respective pixel are shown with the same reference numerals attached thereto and any further explanation is omitted for brevity.

With both the signal readout transistor 602 and reset transistor 603 ON, the photodiode 601 and charge voltage conversion capacitor 604 are set to their initial voltages at a time. Then with the reset transistor 603 OFF, a signal charge photoelectrically converted by the photodiode 601 is stored in the charge voltage conversion capacitor 604. Then with the signal readout transistor 602 OFF, a signal charge at the OFF time is held in the charge voltage conversion capacitor 604. As a result, an electronic shutter's shot is effected in all the pixels at the same time.

At a read time, when the row select transistors 606 are sequentially turned ON, the signal amplifying transistor 605 is rendered active in a row-by-row fashion and a signal voltage is obtained from a signal output line. Even if there is any variation in the threshold voltage of the respective signal amplifying transistor 605, it is cancelled in the following way. That is, a voltage at a signal-present time is output under ON/OFF control and held in a subsequent-stage circuit and, if, in this case, a difference is obtained between a voltage at the signal-present time and a voltage at a signal-absence time, it is possible to obtain only a pure signal.

In the above-mentioned respective embodiment, a light shielding layer is formed in other than the image pickup area so as not to be adversely affected by light coming from an outside.

According to the present invention, a semi-conductor chip is such that an image pickup area suitable to a subject image is secured. And the burden of the signal processing section is alleviated so as to obtain only shot data required. Further, the semi-conductor manufacturing technique can be fully utilized so as to secure the image pickup area on the semi-conductor chip to a requisite minimal extent. In this case, it is not possible to arrange a drive device, signal processing circuit, memory, etc., on a remaining area on the chip. It is, therefore, possible to improve a utilization efficiency on the chip and to reduce a resultant cost required.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

What is claimed is:

1. An area isolation type solid-state image pickup device comprising:
    a semiconductor chip serving as an image pickup element with an image pickup area formed on an element formation of surface the semiconductor chip to correspond to an optical image configuration of a subject, said image pickup area including a first image pickup area corresponding to the optical image of the subject, and a second image pickup area different from the first image pickup area;
    an element drive circuit and processing section formed on a section other than the image pickup area, the processing section being formed to process a signal obtained from the image pickup area; and
    means for switching an image picked-up state from the first image pickup area to the second image pickup area, when an obtained subject image is displaced from the first image pickup area, and for switching the image picked-up state from the second image pickup area to the first image pickup area, when the obtained subject image from the second image pickup area coincides with an initially set image configuration.

2. The area isolation type solid-state image pickup device according to claim 1, wherein a second optical system conducting an optical image to the second image pickup area is wider in angle than a first optical system conducting an optical image to the first image pickup area.

3. The area isolation type solid-state image pickup device according to claim 2, wherein a light path from the second optical system is to be conducted to the second image pickup area, the light path is conducted there from a path displaced from a site above the first image pickup area so as to prevent an interference of light at the first image pickup area.

4. An area isolation type solid-state image pickup device comprising:
    a semiconductor chip serving as an image pickup element with an image pickup area formed on an element formation surface of the semiconductor chip to correspond to an optical image configuration of a subject, said image pickup area including a first image pickup area corresponding to the optical image of the subject, and a second image pickup area different from the first image pickup area;
    an element drive circuit and processing section formed on a section of the image pickup device other than the image pickup area, the processing section being formed to process a signal obtained from the image pickup area; and
    means for switching an image picked-up state from the first image pickup area to the second image pickup area, when an obtained subject image is displaced from the first image pickup area, and for switching the image picked-up state from the second image pickup area to the first image pickup area, when the subject image from the second image pickup area coincides with an initially set image configuration.

5. The area isolation type solid-state image pickup device according to claim 4, wherein a second optical system conducting an optical image to the second image pickup area is wider in angle than a first optical system conducting an optical image to the first image pickup area.

6. The area isolation type solid-state image pickup device according to claim 5, wherein, when a light path from the second optical system is to be conducted to the second image pickup area, the light path is conducted there from a path displaced from a site above the first image pickup area so as to prevent an interference of light at the first image pickup area.

* * * * *

UNITED STATES PATENT AND TRADEMARK OFFICE
CERTIFICATE OF CORRECTION

PATENT NO. : 6,333,760 B1
DATED : December 25, 2001
INVENTOR(S) : Terui et al.

It is certified that error appears in the above-identified patent and that said Letters Patent is hereby corrected as shown below:

<u>Title page,</u>
Item [73], Assignee: please change "Kawasaki Kaisha Toshiba" to -- Kabushiki Kaisha Toshiba --

Signed and Sealed this

Twenty-third Day of July, 2002

Attest:

Attesting Officer

JAMES E. ROGAN
*Director of the United States Patent and Trademark Office*